United States Patent
Mattes (10) Patent No.: US 7,930,112 B2
(45) Date of Patent: Apr. 19, 2011

(54) METHOD FOR EVALUATING MEASURED VALUES FOR IDENTIFYING A MATERIAL FATIGUE

(75) Inventor: Johannes Mattes, Mannheim (DE)

(73) Assignee: Hottinger Baldwin Messtechnik GmbH, Darmstadt (DE)

( * ) Notice: Subject to any disclaimer, the term of this patent is extended or adjusted under 35 U.S.C. 154(b) by 666 days.

(21) Appl. No.: 11/919,107

(22) PCT Filed: Apr. 19, 2006

(86) PCT No.: PCT/EP2006/003569
§ 371 (c)(1),
(2), (4) Date: Oct. 22, 2007

(87) PCT Pub. No.: WO2006/111360
PCT Pub. Date: Oct. 26, 2006

(65) Prior Publication Data
US 2009/0306909 A1  Dec. 10, 2009

(30) Foreign Application Priority Data
Apr. 20, 2005  (DE) .......................... 10 2005 018 123

(51) Int. Cl.
*G01B 5/28* (2006.01)
*G01N 3/00* (2006.01)

(52) U.S. Cl. ........................................... 702/36; 73/795

(58) Field of Classification Search .................. 702/36, 702/33, 34–35, 41–43, 81, 88, 127, 138–139, 702/144, 179–185, 188–189, 193, 199; 73/12.07, 73/760, 781, 783, 787, 788–790, 794–796, 73/798–799, 802, 816, 819, 837, 847–848, 73/852; 374/46, 48–49, 51
See application file for complete search history.

(56) References Cited

U.S. PATENT DOCUMENTS
3,387,120 A * 6/1968 Funk et al. ...................... 701/14
(Continued)

FOREIGN PATENT DOCUMENTS
EP  0 110 865  6/1984
(Continued)

OTHER PUBLICATIONS

Simpson et al., The canadian and Australian F/A-18 International Follow-On Structural Test Project, ICAS 2002 Congress, 17 pp.*

(Continued)

*Primary Examiner* — Eliseo Ramos Feliciano
*Assistant Examiner* — Toan M Le
(74) *Attorney, Agent, or Firm* — W. F. Fasse; W. G. Fasse (57) ABSTRACT

In a method of evaluating measured values for recognizing defect conditions due to material fatigue on aircraft parts, strain sensors (6) are applied on the critical locations of an aircraft (1) and measured values of outputs of the strain sensors are detected at different loading conditions, amplified and stored through several measuring circuits. An evaluating apparatus (9) derives, signals or indicates a material fatigue by comparison of current measured values with previous measured values. The critical aircraft parts (1) are impinged on with prescribed loading conditions by loading elements (3). The strain effect caused thereby is detected by measuring circuits. The evaluating apparatus (9) forms, for at least each loading condition and each measuring circuit, an allocated reference value and a permissible limit value range. If current measured values exceed the limit value range, this represents a material fatigue manifestation.

15 Claims, 6 Drawing Sheets

U.S. PATENT DOCUMENTS

| | | | |
|---|---|---|---|
| 4,215,412 A | 7/1980 | Bernier et al. | 701/100 |
| 4,336,595 A | 6/1982 | Adams et al. | 702/34 |
| 4,480,480 A * | 11/1984 | Scott et al. | 73/769 |
| 4,756,194 A * | 7/1988 | Grandpierre et al. | 73/799 |
| 4,901,575 A * | 2/1990 | Bohannan et al. | 73/587 |
| 5,195,046 A | 3/1993 | Gerardi et al. | 702/35 |
| 5,421,204 A * | 6/1995 | Svaty, Jr. | 73/786 |
| 5,881,971 A | 3/1999 | Hickman | 244/1 R |
| 6,006,163 A | 12/1999 | Lichtenwalner et al. | 702/36 |
| 6,370,964 B1 | 4/2002 | Chang et al. | 73/862.046 |
| 6,480,792 B1 * | 11/2002 | Prendergast | 702/42 |
| 2006/0004499 A1 * | 1/2006 | Trego et al. | 701/29 |

FOREIGN PATENT DOCUMENTS

| | | |
|---|---|---|
| EP | 1 018 641 | 7/2000 |

OTHER PUBLICATIONS

23rd Congress of International Council of the Aeronautical Sciences, Sep. 8-13, 2002, Toronto, Canada, Paper ICAS 2002-0.6, 1 page.*

* cited by examiner

METHOD FOR EVALUATING MEASURED VALUES FOR IDENTIFYING A MATERIAL FATIGUE

FIELD OF THE INVENTION

The invention relates to a method for the evaluation of measured values for the recognition of defect conditions due to material fatigue on aircraft parts.

BACKGROUND INFORMATION

Most of the supporting or carrying structural elements and assemblies in vehicles, cranes, aircraft and the like are not only statically loaded but are also often subject to dynamic loads. In that regard, damages can arise on the structural elements or assemblies not only upon exceeding a static limit load, but also due to a plurality of small dynamic loads, which lead to grain changes in the materials, whereby it can lead to damages due to material fatigue. Especially in the aircraft construction, dynamic loads often arise due to the cyclic loads in the various flight phases, whereby these dynamic loads cause such a material fatigue over a long time span. Therefore, aircraft are routinely inspected or examined for material fatigue damages, after prescribed flight hours, by ultrasonic examinations or x-raying. Such inspections or examinations are very time-consuming and expensive, and should therefore only occur when such damages can be counted on in accordance with expectations.

Therefore, it is attempted already during the development and construction phase, to determine by continuous load tests the critical locations on aircraft parts that can lead to such material fatigue manifestations. Through such continuous load tests it is therefore also possible, for each individual aircraft or its parts, to specify a number of flight hours, after which certain material fatigue tests or examinations shall be carried out, or in total to determine a maximum number of flight hours of an aircraft, after which a further operation is no longer justifiable for safety reasons due to material fatigue manifestations.

For such continuous load tests, in turn very complex or costly testing systems are necessary, through which partially the entire operating life of an aircraft must be simulated, detected and evaluated. For that purpose, up to 7000 strain gages are applied partially on the entire aircraft or on the critical parts thereof, such as fuselage or carrying surfaces, for example. In that regard, each individual strain gage is usually embodied as a quarter bridge and is supplemented with further supplemental resistances to form a Wheatstone measuring bridge, and is connected with an amplifier channel of an amplifier apparatus by a three to six wire measuring line or cable. By such an amplifier apparatus having up to 7000 channels, the individual measuring signals are amplified and digitized, and are then stored in a following memory and calculating or processing circuit, and are indicated or displayed or signaled as measured values. In a continuous load test, the aircraft to be inspected or its individual parts are now acted or impinged on by a usually hydraulic loading apparatus, with an alternating load that is modeled on the flight operation. In that regard, then both the introduced forces as well as the strains caused thereby on the aircraft parts are detected in time sequences and are stored for the evaluation. Then material fatigue manifestations can be determined from the corresponding strain progression or course on the critical aircraft parts after a plurality of alternating loadings.

In a comparatively overseeable or manageable loading test of, for example, 1000 different load conditions with only 2000 measuring channels or strain measuring points, then at least two million data sets will need to be evaluated, which necessitate a high investment or application of personnel and time for a manual evaluation, in order to derive therefrom an evaluation for the recognition of material fatigue manifestations.

Such an apparatus for the monitoring of the structural fatigue of aircraft and the parts thereof is known from the EP 1 018 641 B1. For that purpose, with the aid of instruments present in the aircraft, the magnitude and the number of turbulence events, the magnitude and the number of the G-loads arising due to flight maneuvers, the number of pressure loading cycles arising in the aircraft, the number of take-off and landing cycles, as well as the number of the wing flap cycles, are detected and stored. These data can be read out by the aircraft or maintenance personnel for the evaluation of fatigue manifestations. However, due to manual evaluation, only a preventive inspection or examination for material fatigue damages can be initiated from the number and the staggered magnitude indications or data, and a defect condition is only then recognizable from the preventive inspection or examination.

From the EP 0 110 865 A2, a measuring apparatus is known for the monitoring of the degree of damage due to material fatigue also on aircraft. For that purpose, several sensors are arranged on the critical locations of the aircraft and the like to be monitored, which sensors detect the material loading and then supply these signals respectively through a separate amplifier channel of a sample and hold circuit and a common multiplexer circuit. An analog-digital converter is connected at the output of the multiplexer circuit, and the analog-digital converter supplies the signals to a comparator, which compares the signals with extreme values stored in a buffer memory. By means of a counter or a summing memory of an evaluating circuit, especially from the extreme values of the signals, a cumulative loading signal is formed, stored and therefrom a degree of damage is calculated. This determined degree of damage is then continuously compared with a prescribed acceptable or permissible degree of damage, and upon exceeding the same is signaled or indicated. This method is, however, only suitable for monitoring the degree of damage of an aircraft that is in operation, for which a prescribable permissible degree of damage must previously have been determined, which is only determinable by complex or costly continuous loading tests on comparable aircraft parts. For that purpose, on the basis of such a continuous loading test, a Woehler stress-cycle diagram with damage lines is produced, albeit manually, from which corresponding limit load cycle criteria depending on the loading magnitude are recognizable, and which serve for the determination of the permissible degree of damage.

SUMMARY OF THE INVENTION

Therefore, the object underlies the invention, to provide a method by which defect conditions are recognized quickly and very accurately in continuous loading tests, which, in the operating condition, can lead to damages due to material fatigue on aircraft parts and the like.

This object is achieved by the invention in a method of determining an occurrence of a material fatigue manifestation in at least one of plural aircraft components of an aircraft due to material fatigue during fatigue testing of the aircraft components, comprising the steps:
a) by externally acting on the aircraft with a plurality of externally acting loading elements, imposing on the aircraft components a plurality of prescribed loading conditions in successive loading cycles, thereby causing strains in the aircraft components;

b) detecting the strains with strain gages arranged on the aircraft components, and with the strain gages producing strain gage outputs representative of the strains;

c) evaluating the strain gage outputs to determine therefrom measured strain values respectively successively in the successive loading cycles and respectively allocated to the strain gages;

d) for each one of the loading conditions for each one of the strain gages, respectively establishing a reference value based on at least a first one of the measured strain values arising in a first one of the successive loading cycles;

e) specifying a permissible deviation;

f) for each reference value, determining an absolute limit value range based on the permissible deviation relative to the reference value;

g) comparing the measured strain values to the absolute limit value range, respectively for each one of the loading conditions for each one of the strain gages; and h) if the comparing in the step g) determines that at least one of the measured strain values falls outside of the absolute limit value range, then in response thereto determining, signaling or indicating that a material fatigue manifestation has occurred in at least one of the aircraft components.

The invention has the advantage, that the evaluation of measured values for the recognition of defect conditions due to material fatigue on aircraft or the parts thereof occurs automatically through an electronic evaluating apparatus. In that regard, the evaluation begins already with carrying out prescribed load conditions, with which the critical aircraft parts are loaded and which bring about strain manifestations on the aircraft parts, which strain manifestations are advantageously detected with a plurality of measuring locations. In that regard, especially the time duration after which the defect conditions of a fatigue manifestation can already be recognized is especially of advantage, which is already possible after completion of the first repetition of a certain loading condition by comparison of the individual measured values.

The invention furthermore has the advantage that the defects due to fatigue manifestations are determinable directly by a strain measurement on the critical aircraft parts, without further measurements for the analysis of the material structure, for example by ultrasound or x-rays, being necessary, or without Woehler strain-cycle diagrams needing to be established. On the basis of the contemporaneous measurements of the strain and the evaluation thereof, the necessary testing duration can be reduced to a minimum, whereby advantageously the cost or complexity of long term tests can be considerably reduced. Moreover the invention still further has the advantage that defect conditions due to fatigue manifestations can be detected already so early by exceeding of prescribable limit values, linear deviations, or trend progressions, before an actual occurrence of damage, and are immediately preventable by cost-advantageous or economical structural changes, and similarly can be newly evaluated upon continuation of the test run.

Through the contemporaneous evaluation of the loading conditions with respect to their effects on determined fatigue manifestations, even very accurate necessary aircraft inspection intervals or a maximum permissible durability can advantageously be specified, which permits longer examination intervals due to the evaluated loading conditions than this is possible on the basis of experience values with consideration of necessary safety aspects in air flight traffic.

In a particular type of embodiment of the evaluating method it is provided to support the evaluation at first on the individual measured value comparison, and with increasing test duration to also take into account statistical evaluations, trend considerations, and additionally linearity effects, by which the evaluation accuracy is continuously increasable, in order to make possible an unambiguous and secure defect recognition of fatigue manifestations already before the occurrence of damage, without requiring the testing structure to be changed or the testing run to be interrupted. Such an evaluation of measured values for the recognition of defect conditions due to fatigue manifestations is not only suitable for evaluating or rendering an opinion on new construction parts, but rather also for the estimation of a remaining operating life of used aircraft or their parts. In that regard, in a further particular type of embodiment of the evaluation method, it is advantageous that especially small strain measured values remain unconsidered for the evaluation, when the measurement errors thereof are at least equal to or greater than the limit value ranges for recognition of the fatigue manifestations, whereby a secure and accurate defect recognition is first made possible.

BRIEF DESCRIPTION OF THE DRAWINGS

The invention is further explained in connection with example embodiments that are shown in the drawing. It is shown by.

DETAILED DESCRIPTION OF EXAMPLE EMBODIMENTS OF THE INVENTION

Figure 1:
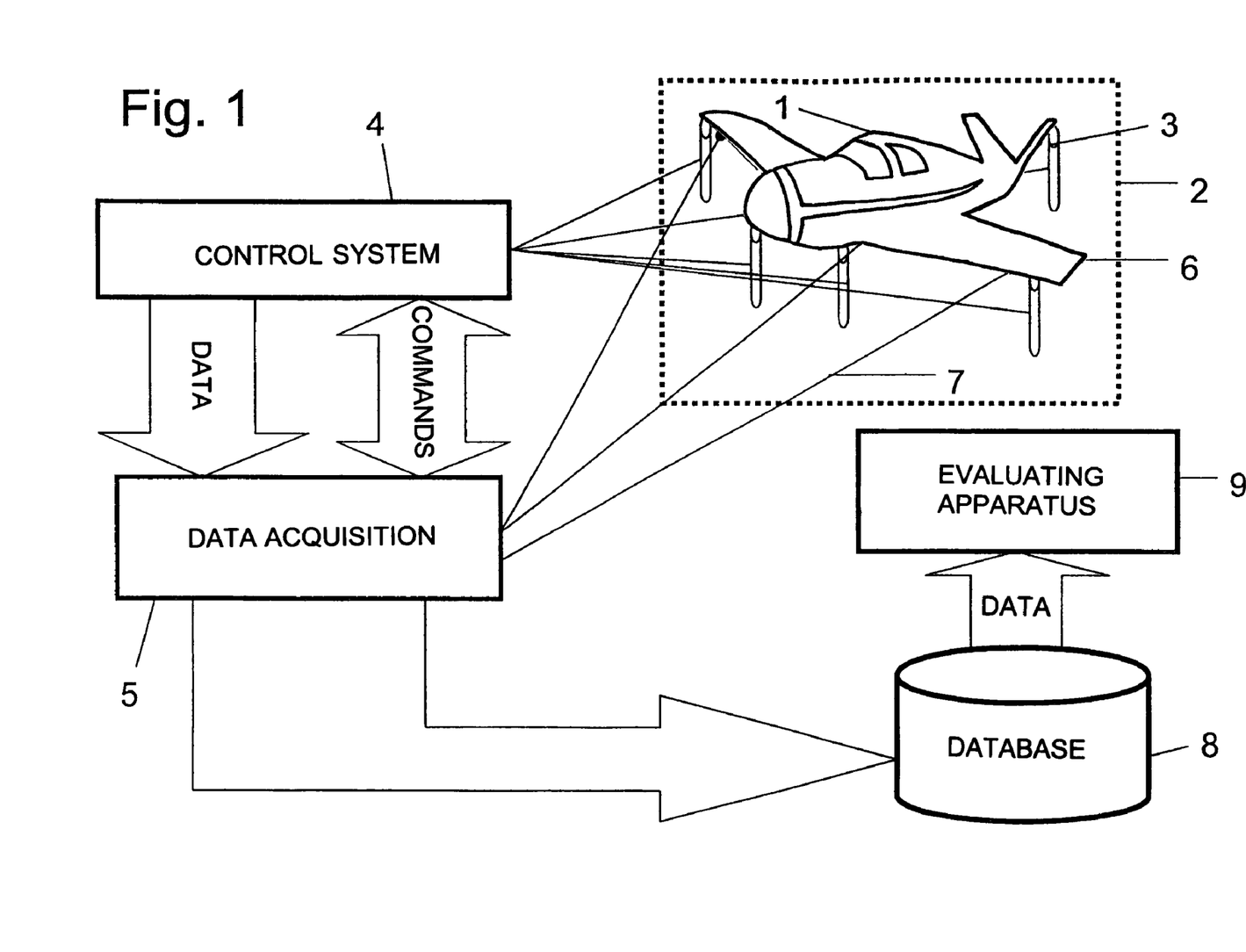
FIG. 1: a schematic measuring arrangement for the recognition of defect conditions due to material fatigue on aircraft or the parts thereof.

A measuring arrangement for the recognition of defect conditions due to material fatigue on aircraft or parts thereof is schematically illustrated in FIG. 1 of the drawing. For that purpose, the entire aircraft 1 to be examined or parts thereof is arranged on a test stand apparatus 2. In that regard, the aircraft 1 is supported or braced on a representative number of loading elements 3, which are preferably embodied as hydraulic cylinders. In that regard, the hydraulic cylinders are arranged so that they can simulate the loading of an aircraft 1 in the operating condition, in a manner that is as true to reality as possible. For that purpose, for the illustrated fighter aircraft, typically about 120 hydraulic cylinders 3 are provided, by means of which about 1000 different loading conditions can be actuated. An electronic control system 4 is provided for the control of these loading conditions, and the control system 4, through a program-controlled regulating hydraulic system, actuates the 1000 different loading conditions in a prescribed sequence over a longer period of time, of partially up to one year, by which approximately the flight loading of a fighter aircraft during its entire operating lifetime of about 2000 flight hours can be recreated.

Force sensors are additionally provided in the hydraulic cylinders 3, with which force sensors the introduced loading values are individually detected and are introducible in a regulated manner corresponding to a nominal or desired value pre-specification. For that purpose, corresponding control commands are transmitted from a data acquisition apparatus 5 to the control system 4, and the hydraulic cylinders 3 are correspondingly operated or actuated. The force sensors arranged in the hydraulic cylinders 3 are electrically connected with the control system 4, so that for each loading condition, the introduced force of each hydraulic cylinder 3 is available as a loading value, and these data can be queried or polled through the data acquisition apparatus 5.

Moreover, strain gages 6 are applied as strain sensors on the preferably critical aircraft parts, with which strain gages the surface strain for a prescribed loading condition is detected. For that purpose, partially up to 7000 strain gages 6 are applied on an aircraft or on an aircraft part, and the strain gages are connected by a three- to six-wire measuring line or cable 7 with the data acquisition apparatus 5. The data acquisition apparatus 5 preferably still further contains the supplemental resistances, that form a Wheatstone measuring bridge circuit with the strain gages 6. Each measuring bridge circuit is connected with a separate amplifier channel in the data acquisition apparatus 5, and the amplifier channel amplifies the detected strain measurement signals and digitizes them in a following analog-digital converter, and all together forms a measuring channel or a separate measuring circuit. In a conventional testing cycle of about 1000 different loading conditions with preferably 2000 measuring circuits, thus at least two million measurement data sets are formed, which must be evaluated for the defect evaluation and determination. Therefore, the data sets of the measurement signals detected in time sequence are stored in an electronic database 8, that is embodied as a server or PC (personal computer).

For the analysis and evaluation of the measured values, the database 8 is connected with a program-controlled electronic evaluating apparatus 9, which computationally evaluates the detected or acquired measurement data sets or measured values largely contemporaneously and through coupling with previous measured data sets, in order to recognize therefrom defect conditions that have arisen or future defect conditions due to material fatigue on critical aircraft parts.

For that purpose, at the beginning or start of a testing process, a previously determined program-controlled loading condition is actuated by the control apparatus 4 by means of the hydraulic cylinders 3, by which loading condition a prescribed loading is introduced into the aircraft 1 or the parts thereof, whereby the loading shall correspond to a certain flight condition. In that regard, the individual hydraulic cylinders 3 are generally actuated with different loadings, because in flight operation the aircraft parts are also subjected to different loading conditions. The strains arising on the critical aircraft parts with this first loading condition are detected by the individual strain gages 6 simultaneously or contemporaneously, or synchronized, in the plurality of the measuring channels as a first measured value line of a certain loading condition, and are stored in the database 8.

Figure 2:
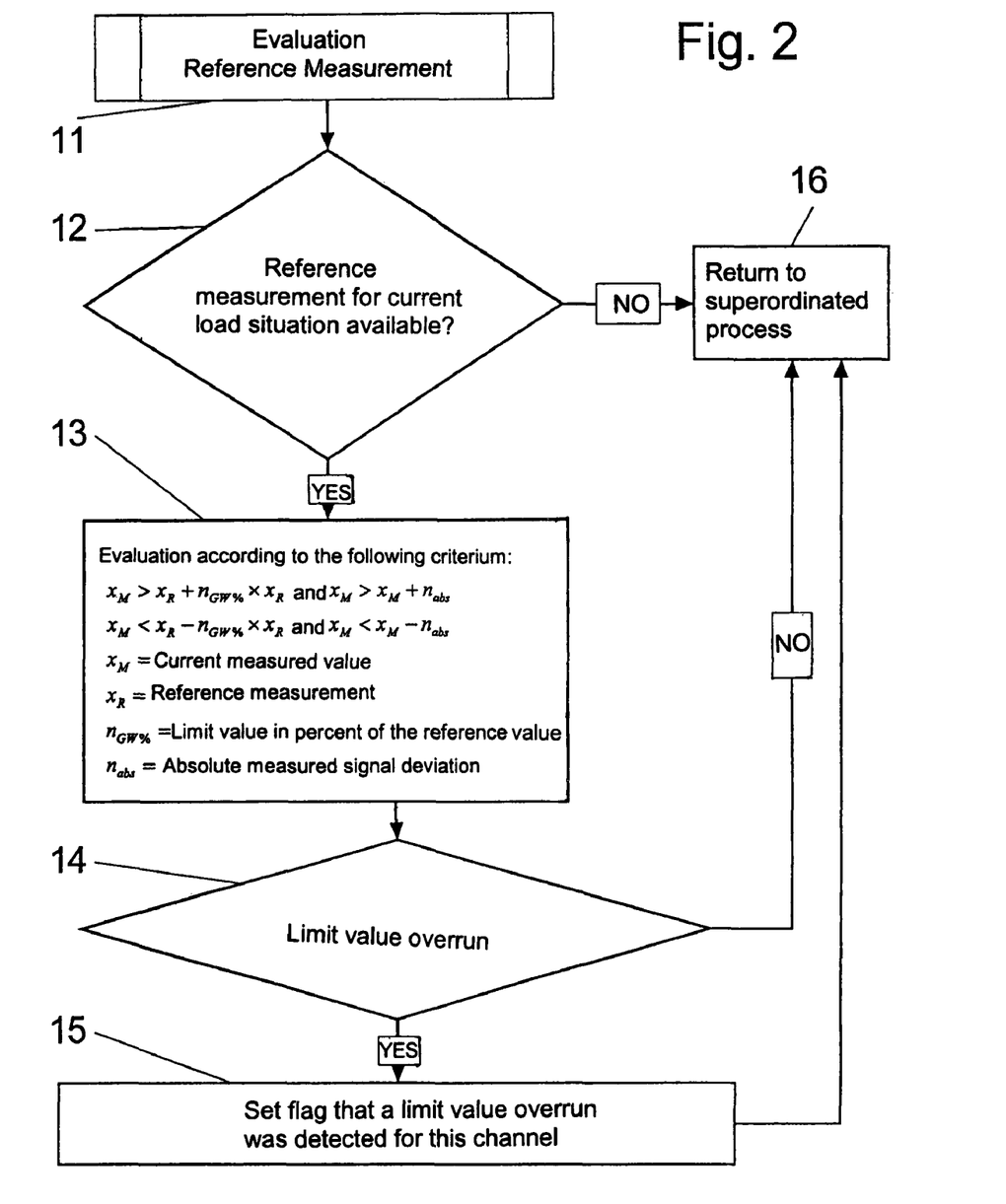
FIG. 2: a signal flow diagram for the evaluation of individual measured values by comparison with a previous reference measured value.

The beginning or start of an evaluation of the measured values $X_M$ through individual comparison is illustrated in FIG. 2 of the drawing. In the start step 11, the evaluation method starts through reading out the measured values or the measured data sets out of the database 8, and, after the reference measurement in the program step 12, the evaluating apparatus 9 forms therefrom in the calculating step 13 first reference values $X_R$ of a respectively allocated measuring channel, which is allocated to a spatially or locally identifiable strain measurement area and thereby detects or acquires the strain on a critical aircraft area as a result of the loading. Simultaneously, in the evaluating apparatus 9, through the calculating step 13 a limit value range $n_{GW\%}$ is defined from the reference measurement for the current or present loading condition, and the deviation of the limit value range shall not yet represent a defect condition as a result of a fatigue manifestation. Such a limit value range $n_{GW\%}$ can be prescribed by the respective testing personnel, depending on the test object, as a relative magnitude of, for example, small $n_{GW\%}=\pm 3\%$. From that, the evaluating apparatus in the calculating step 13 calculates, for example for a measured value $X_M$ of 30 mV/V, an absolute limit value range of ±0.9 mV/V.

In this manner, a prescribed number of prescribed loading conditions are actuated after one another in time, and the respective associated measured values $X_{Mi}$ are stored in the database 8, and are evaluated in the evaluating apparatus 9 as first reference measured values $X_R$ in the program step 12, and particularly so long until individual prescribed loading conditions are repeated. If the evaluating apparatus 9 in the program step 12 has determined that a loading condition is repeated, and a reference value $X_R$ is available for the corresponding current loading situation or case, then it compares the new current measured values $X_M$ of each measuring channel with the reference values $X_R$ of the same previous loading condition in the evaluating step 14. If a new current individual measured value $X_M$ exceeds the defined reference limit value range, then this is signaled for the respective measuring channel by setting a flag or marker in the program step 15, or is indicated at a different location by a return step 16. Since a plurality of equal loading conditions are always repeated in continuous long-term loading tests, then for example, upon the continuous exceeding of a limit value range after a certain repetition number of the respective loading condition, a conclusion of a defect condition due to fatigue manifestation of the applicable application area can be drawn. Therefore, not only the value of the limit value excess or overrun, but rather preferably also the number of the similar loading conditions that have been carried out, for which the limit range excess or overrun has been determined, are indicated or displayed for the exceeding or overrunning of the reference limit range upon comparison of the individual measured values $X_M$.

Figure 3:
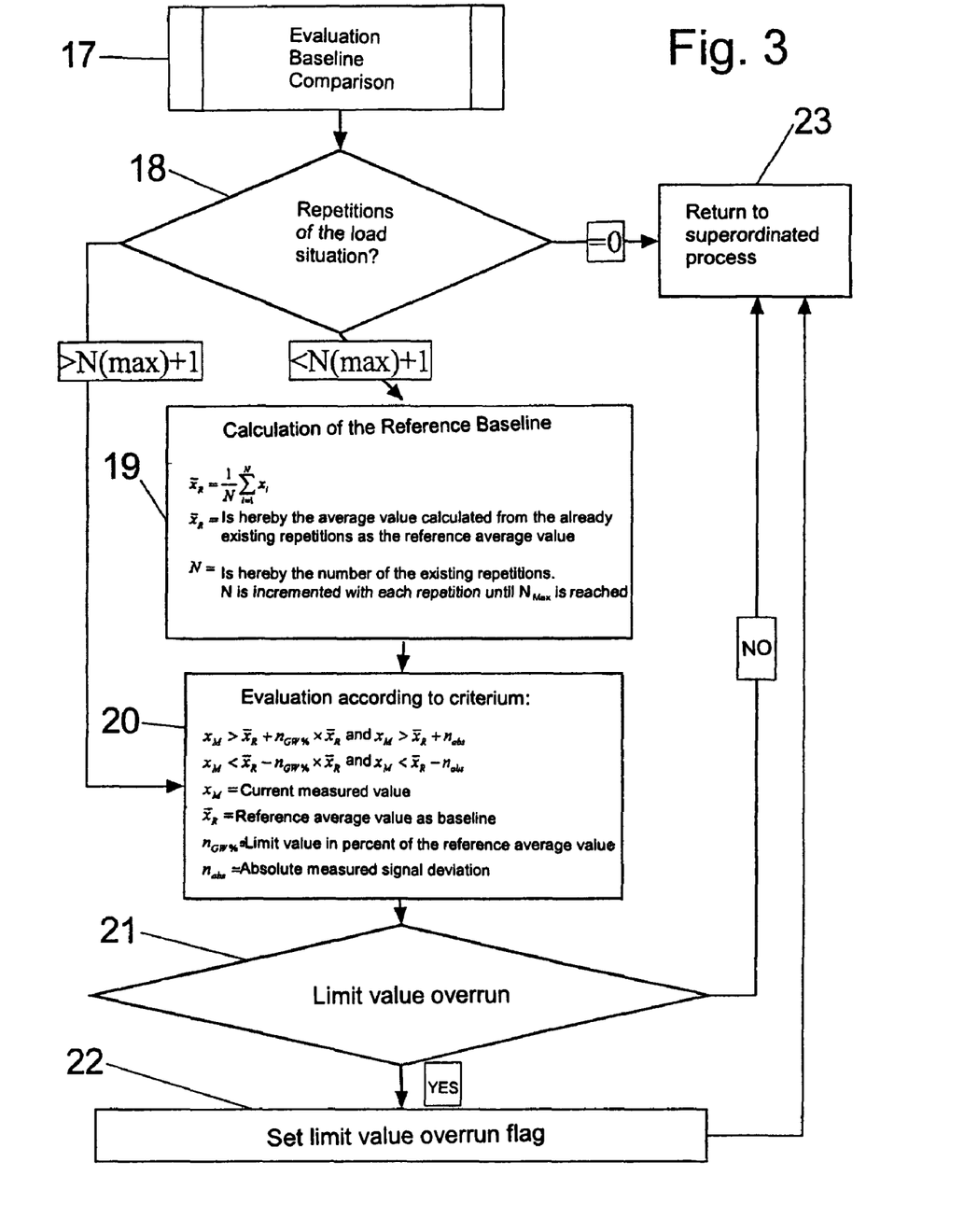
FIG. 3: a signal flow diagram for the evaluation of individual measured values by comparison with a statistically determined mean reference base value.

For improving the accuracy in the specifying or determination of the reference value $X_R$, the evaluating apparatus 9 in a further particular embodiment of the method determines an evaluation according to the so-called baseline comparison on the basis of a statistical number N of previous measurements, which is illustrated in FIG. 3 of the drawing. For that purpose, before a start step 17, a statistical number N of measurement repetitions in the repeat step 18 of one or more loading conditions is prescribed to the evaluating apparatus 9, which are then provided for the calculation of a reference value $\overline{X}_R$. Therefore, during the evaluating process all measured values $X_M$ are summed up for the calculation of the reference baseline of a certain load condition in the calculating step 19, so long until the number N of the measuring repetitions of, for example, N=10 is reached. From that the evaluating apparatus 9 in the calculating step 19 then forms, through averaging or mean value formation of the individual measured values $X_M$, an average reference value $\overline{X}_R$ or a reference baseline. For this purpose, subsequently with the aid of a prescribed limit value range $n_{GW\%}$ of for example ±3%, in a further calculating step 20, an absolute limit value range is still additionally formed, in the measured value range of which no fatigue manifestations shall be determinable.

After carrying out a further measured value repetition following the formation of the reference baseline at, for example, the eleventh measured value repetition of a certain loading condition, the evaluating apparatus 9 in the evaluating step 21 compares the respective current measured value $X_{M11}$ of a certain measuring channel with the average reference value $\overline{X}_R$ calculated for this measuring channel. If this eleventh measured value $X_{M11}$ of a certain loading condition exceeds the determined limit value range of the average reference value $\overline{X}_R$ in the evaluation step 21 then this is evaluated by the evaluating apparatus 9 in the marker or flag step 22 as a determination of a fatigue condition of the applicable measuring channel, and is signaled or displayed or indicated at a different location after or according to the return step 23. Through such a method sequence or progression, a considerable accuracy improvement of the reference value $\overline{X}_R$ is achieved, which would still be subject to a considerable fluctuation range, especially at the start of a measuring run or row through the formation of the reference value $X_R$ from an individual measured value $X_M$. Therefore, through the formation of a reference average value $\overline{X}_R$, the evaluation accuracy is considerably improved.

Figure 4:
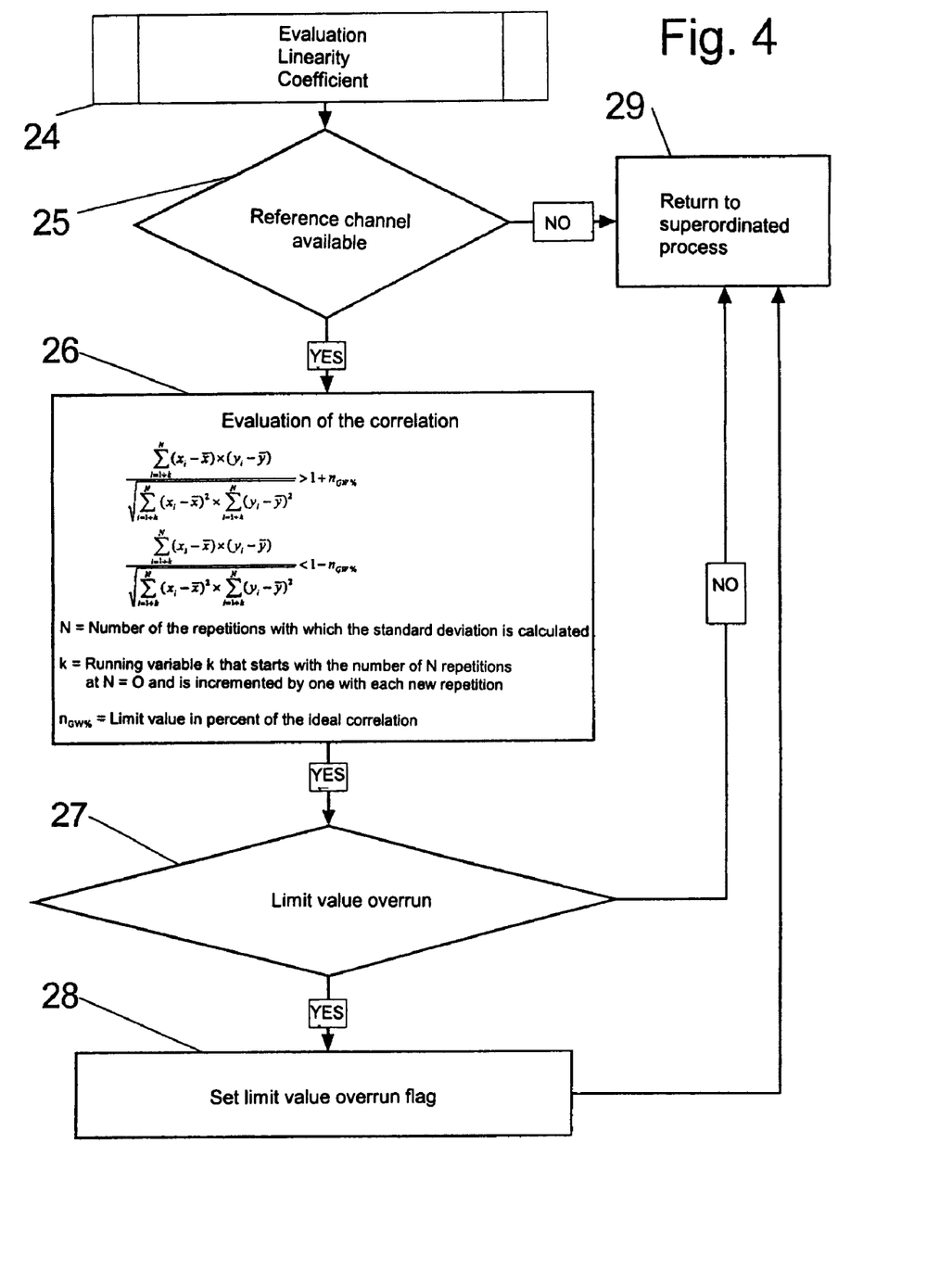
FIG. 4: a signal flow diagram for the evaluation of deviations of the linearity coefficients.

Through a further evaluation of the measurement results, a defect condition due to fatigue manifestation can also be determined with the aid of the evaluation through linearity coefficients, which is illustrated in the signal flow diagram in FIG. 4 of the drawing. The evaluation scheme is based on the recognition that the loading introduced in a certain aircraft area 1 through a certain hydraulic cylinder 3 with the strains detected in this area must be linear so long as no damage due to material fatigue has arisen. For that purpose, after the start step 24, the force $Y_i$ introduced by each hydraulic cylinder 3 is detected in the storage step 25, preferably continuously for different loading conditions as a reference channel, and stored in the database 8. Simultaneously for this reference channel also the associated strain measured value $X_i$ of a certain measuring channel or measuring circuit is stored, which is arranged in the area of a critical aircraft part, which is loaded by the respective hydraulic cylinder 3. Through the evaluating apparatuses 9, these values can be set into a ratio and thus form a linearity factor which must remain constant within certain prescribed limit values $n_{GW\%}$, as long as no fatigue has arisen in the monitored aircraft parts.

For increasing the evaluation accuracy, the linearity coefficients $K_L$ are, however, referenced to a statistical averaging or mean value formation, as is illustrated in the calculating step 26, in which a loading average or mean value $\overline{Y}$ and strain average or mean value $\overline{X}$ are calculated, for example, from the first N=10 successively carried out load values $Y_i$ and the associated 10 strain measurements $X_i$ by the evaluating apparatus 9. These linearity coefficients $K_L$ are set into a ratio in the calculating step 26 according to the following formula:

$$K_L = \frac{\sum_{i=1+k}^{N}(x_i-\overline{x})\times(y_i-\overline{y})}{\sqrt{\sum_{i=1+k}^{N}(x_i-\overline{x})^2 \times \sum_{i=1+k}^{N}(y_i-\overline{y})^2}}$$

and give the linearity coefficient $K_L$=1 for fatigue-free aircraft parts. Only for a certain limit value deviation $n_{GW\%}$ of such an ideal correlation of $K_L$=1 is the existence of a fatigue manifestation on the corresponding aircraft parts determinable. For that purpose, in the evaluating apparatus 9 a prescribed limit value range $n_{GW\%}$ of for example $n_{GW}$=±3% is still calculated, which indicates the correlation range about 1, where no fatigue manifestations have yet arisen. If now in a further measurement a certain deviation from these average values $\overline{X}$, $\overline{Y}$ is determined, which give a correlation range that lies outside these limit values $n_{GW}$, then a non-linearity is determined in the evaluating step 27, and for this current measured value pair $X_i$, $Y_i$ and the associated measuring locations, in a marker or flag step 28 a so-called marker or flag is set, which can be indicated or displayed or signaled at a different location through a return step 29.

Figure 5:
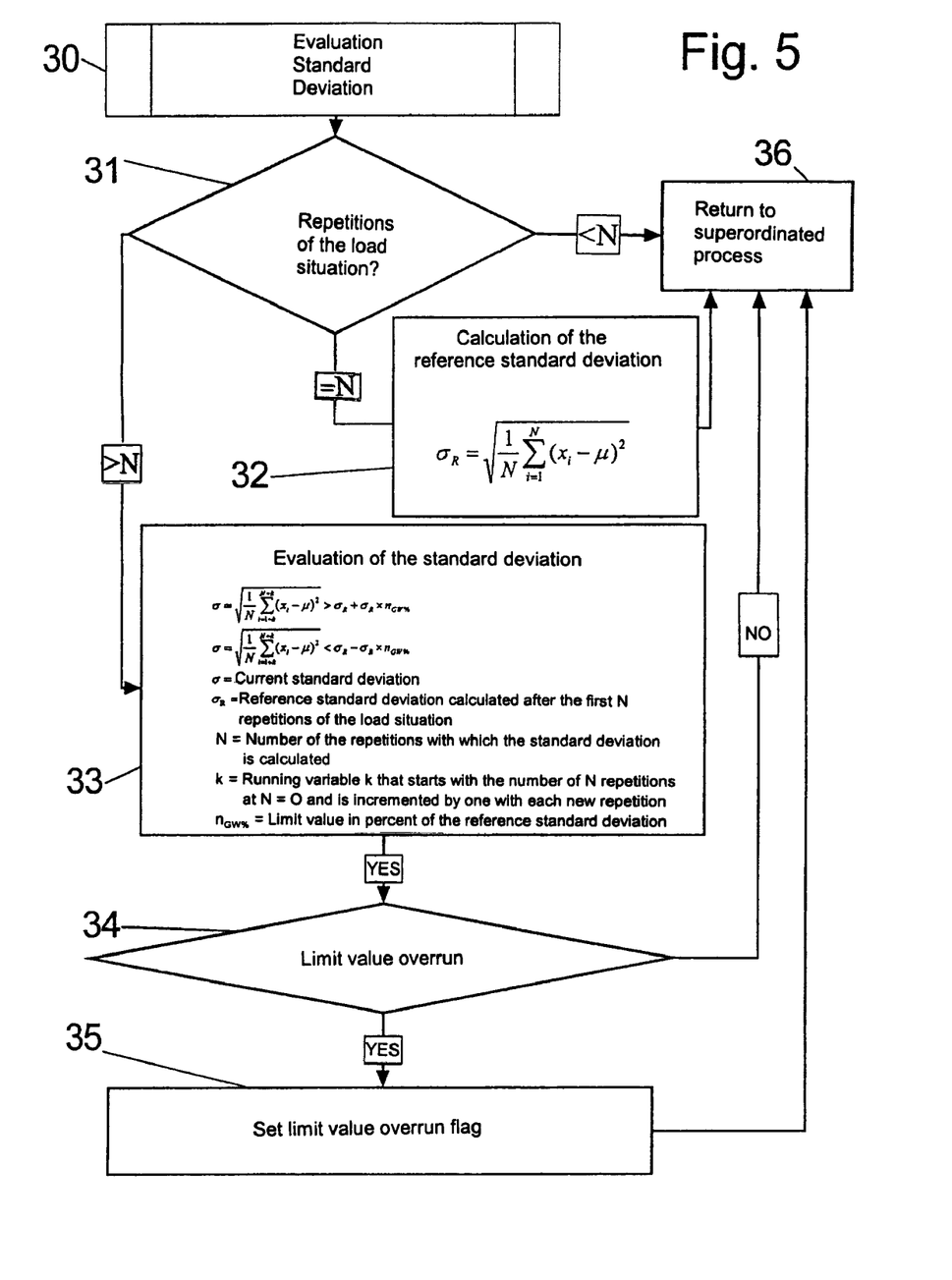
FIG. 5: a signal flow diagram for the evaluation of the current or present standard deviation through comparison with a reference standard deviation.

In such a testing process on aircraft parts 1, in a further embodiment of the method, a defect condition due to fatigue manifestations can also be determined through a change or variation of the standard deviation, as this is illustrated in the flow diagram according to FIG. 5 of the drawing. For that purpose, after a prescribed number N of for example N=10 strain measured values $X_i$ that have been determined on the basis of ten repeated loading conditions of a respective measuring channel, therefrom a standard deviation a is calculated as a reference standard deviation according to a known statistical calculation method in the calculating step 32 by the evaluating apparatus 9. By prescribing a permissible reference standard deviation range $n_{GW}$, two limit values $n_{GW}$ of for example $n_{GW\%}$=±3% are formed from the calculated reference standard deviation $\sigma_R$ in the evaluating apparatus 9 in a further calculating step 33, whereby no defect condition due to material fatigue shall be determined for the two limit values.

Similarly, after each further completed measuring process, once again the evaluating apparatus 9 determines, for a certain number of previous loading conditions, respectively a present or current standard deviation $\sigma$ according to the same statistical calculation method in the calculating step 33, and the current standard deviation is compared with the reference standard deviation $\sigma_R$ in the evaluating step 34. If the current standard deviation $\sigma$ exceeds the calculated limit values $\sigma_{GW}=\pm\sigma_R \times n_{GW}$ for the reference standard deviation $\sigma_R$, then the setting of a marker or flag is carried out through the evaluating apparatus 9 in the marker or flag step 35, whereby the marker or flag effectuates a corresponding signaling or an indication or display in an indicator or display apparatus in a further return step 36, which indicates a defect condition due to material fatigue on a certain measuring channel after a determined number of loading conditions.

Figure 6:
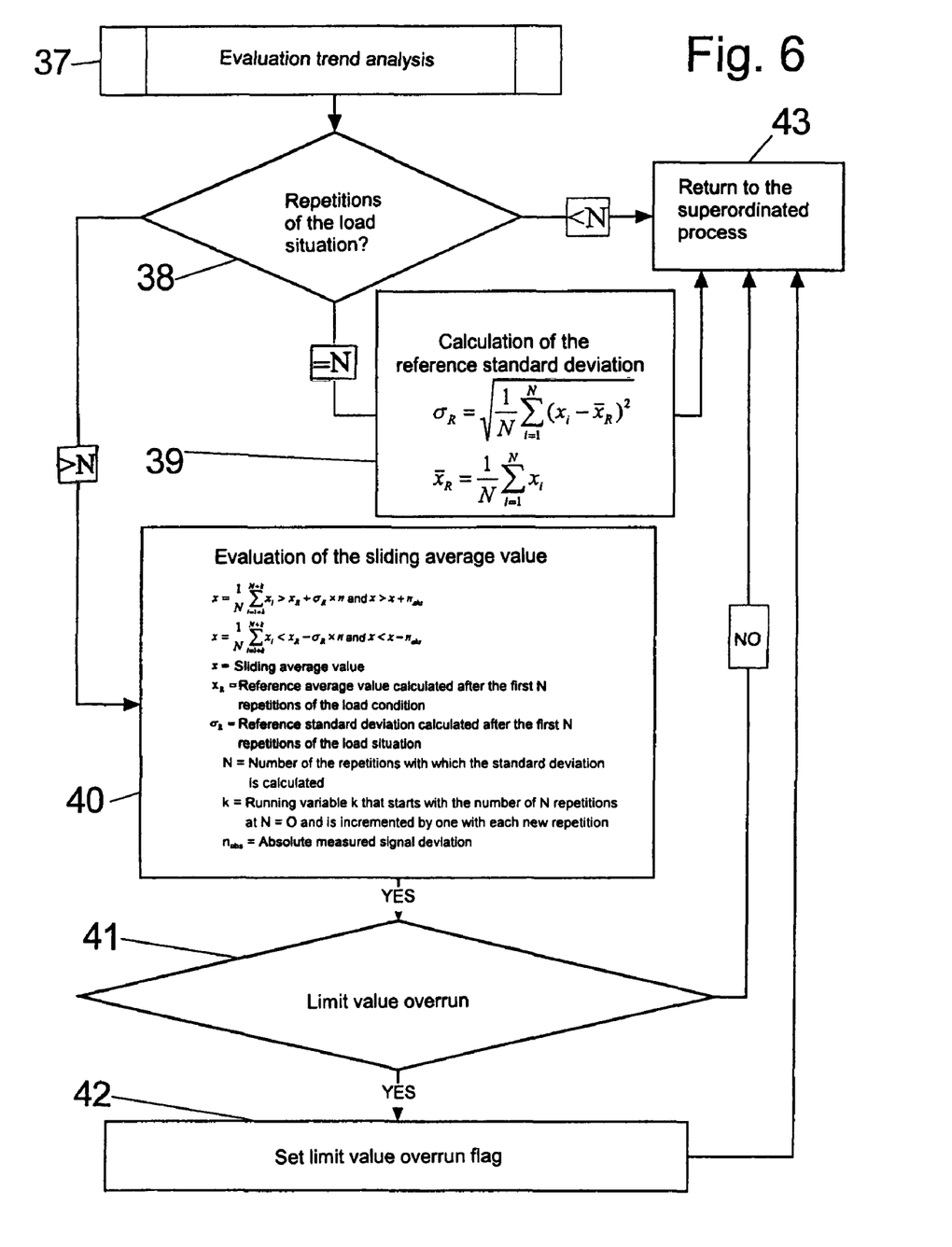
FIG. 6: a signal flow diagram for the evaluation of the trend of a measured value progression or course.

In that regard, already during the course or progress of the test, for the further evaluation of the strain measurement results, an evaluation of a trend of fatigue manifestations in certain measuring channels can be determined, which are illustrated in the flow diagram in FIG. 6 of the drawing. Thereafter, at first according to or after the start step 37, a reference mean or average value $\overline{X}_R$ and from that a statistical reference standard deviation $\sigma_R$ is calculated in the evaluating apparatus 9 according to calculating step 39, from preferably at least N=10 repeated measurements according to a repeat step 38 of a certain loading condition of one measuring channel. For this reference standard deviation $\sigma_R$, the evaluating apparatus 9 with the aid of a prescribed multiple n of the standard deviation $\sigma_R$ in a further calculating step 40 determines, for a standard deviation range of for example $n\cdot\sigma_R$, a standard deviation limit range. Then in the calculating step 40, a sliding mean or average value $\overline{X}$ is calculated by the evaluating apparatus 9 from the following further measured values $X_i$, whereby this average value for example is formed or arises respectively from the last 10 measured values $X_i$. This sliding average value $\overline{X}$ is then compared continuously with the standard deviation range in the evaluating step 41 in all further repetition measurements. In that regard, a clear trend with respect to the fatigue manifestations is derivable already from the course or progression of this determined sliding average value $\overline{X}$. However, as soon as the sliding average value $\overline{X}$ exceeds or leaves the prescribed standard deviation range, then this is a clear indication that a fatigue manifestation arises in the applicable measuring channel or the detected critical aircraft area 1, whereby this fatigue manifestation can lead to a damage in the further progression. Upon exceeding of the calculated limit range by the sliding average value $\overline{X}$, therefore the limit value excess or overrun is marked in a further marker or flag step 42 and transmitted to a signaling or indicating or displaying apparatus in a return step 43. Thus, already during the course or progression of the testing, a possible fatigue damage can largely be prevented or simultaneously structural or constructive measures can be provided by which a fatigue damage is prevented. Moreover, through such a fatigue recognition, already during the progression of the test, a cost-intensive long term test can be shortened which would otherwise have been continued up to one year.

Especially through a coupling of the above trend determination with the linearity deviation, for such complex structural parts as in the aircraft field, a differentiation of static overloads to fatigue manifestations or other defect sources can surely be immediately determined.

In a particular embodiment of an evaluating method, the recognition of defect conditions due to material fatigue is especially improved in that prescribed measured value deviations especially for small strain measured values are not taken into consideration insofar as they lie below the measured value accuracy. A considerable advantage of the invention is that, for such type of multi-location measurements of usually several thousand measuring locations or measuring channels, the prescribed acceptable or permissible limit ranges are mostly prescribable only globally through a relative limit value, from which the evaluating apparatus 9 calculates an absolute limit value or limit value range for each reference measured value and measuring channel, and simultaneously compares the respective current measured values with these during the course or progression of the test. Since due to the plurality of the loading conditions on the measuring locations partially only very small measured values can be detected or acquired, of which the measuring inaccuracy however can lead to higher deviations than the permissible limit value deviation, it normally gives rise to an abundance of limit value excesses or overruns, which however basically do not yet represent a defect condition with regard to material fatigue. Therefore, for each measuring channel, on the basis of a known measuring inaccuracy, an absolute measuring signal deviation of for example ±0.5 mV/V is provided, which is respectively compared with the relative limit value deviation $n_{GW\%}$ of ±3% and the absolute limit value deviation of for example ±0.9 mv/V calculated therefrom. In that regard, then only those deviations are taken into consideration for the defect recognition, of which the limit value range is absolutely larger than the permissible measuring inaccuracy deviation. This leads especially to a clearer evaluation through the higher measured values that are particularly decisive for the determination of the material fatigue.

An especially advantageous embodiment of the evaluation method is given in the rapid evaluation of the many thousand-fold measured values, which begins for the multi-fold loading conditions immediately after the first repetition of a certain loading condition through individual comparison with the first measured value available as the reference value. Whereby simultaneously the calculation of average values is started by the evaluating apparatus 9 with further repetitions of loading conditions, which makes possible a statistical evaluation and a trend recognition, so that through the coupling of all evaluation methods through the continuous measured value enlargement or increasing, a multi-fold increasing evaluation accuracy for the recognition of defect conditions due to material fatigue arises. Thereby, a very accurate defect recognition due to material fatigue is possible with a minimum testing duration. Especially it is possible only with such a method, in a justifiable time, to evaluate such a plurality of measuring locations and measured values for material fatigue manifestations, and from that to indicate a sure prognosis of the necessary monitoring or testing intervals or of expected total operating life of similar aircraft or their parts, which especially take into consideration the necessary safety requirements of air travel.

Such an evaluating method can also be used for material tests for material fatigue for structures outside of the air and space travel, whereby the variety or diversity and the complexity of the structural parts basically first arises from the opposed goals of the air and space travel, according to which the parts shall comprise a minimum weight and for safety reasons must withstand all possible operating conditions for a prescribed operating life. It is first the diversity or variety of these mutually opposed objects that requires such a complex testing and evaluating arrangement, in order to surely recognize material fatigue manifestations on aircraft or their parts.

The invention claimed is:

1. A method for evaluation of measured values for the recognition of defect conditions due to material fatigue on aircraft parts, in which strain sensors (6) are applied on the critical locations of an aircraft (1) or its parts, whereby the measured values of the strain sensors are detected at different loading conditions through several measuring circuits, are amplified, and are stored, and from which an evaluating apparatus (9) derives, signals or indicates a material fatigue through comparison of current measured values with previous measured values, characterized in that the critical aircraft parts (1) are impinged on with a plurality of prescribed loading conditions by a plurality of externally acting loading elements (3), and in that the strain effect caused thereby is detected through a plurality of measuring circuits including strain gages as the strain sensors, and the evaluating apparatus (9) for at least each loading condition and each measuring circuit forms an allocated reference value and a permissible limit value range, whereby, according to the detected strain measured values ($X_M$) for each loading condition, from at least the first existing current measured values for each measuring circuit these are evaluated as reference values ($X_R$) and therefrom an absolute limit value range is calculated for each reference value ($X_R$) through prescription of a permissible deviation ($n_{GW\%}$), which limit value range is subsequently coupled with the current measured values so that the exceeding of the limit value range by at least one current measured value represents occurrence of a material fatigue manifestation.

2. The method for evaluation of measured values according to claim 1, characterized in that, for the force introduction in the carrying out of the different loading conditions, at least 10 loading elements (3) are provided on the aircraft parts to be tested, and in that for the detection of the caused strain effect on the critical aircraft parts at least 100 strain sensors (6) are applied and are connected with at least 100 measuring circuits, whereby the loading elements (3) are actuated by a control system (4), and the measured values are cyclically detected by a data acquisition apparatus (5), amplified and digitized and are evaluated by a connected evaluating apparatus (9) for the recognition of material fatigue manifestations already during carrying out the testing process.

3. The method for evaluation of measured values according to claim 1, characterized in that the detected strain measured values from the strain sensors (6) and the detected load measured values from the loading elements (3) are intermediately stored in a database (8) and are read out for the evaluation by the evaluating apparatus (9) and are coupled with one another in a program-controlled manner.

4. The method for evaluation of measured values according to claim 1, characterized in that, from the current strain measured values ($X_M$) after each repetition of a certain loading condition these are compared with the associated reference measured values ($X_R$) and upon exceeding the respective limit value range determined therefor this is evaluated as material fatigue manifestation for the applicable measuring circuit.

5. The method for evaluation of measured values according to claim 1, characterized in that, for the repetition of certain loading conditions, the associated strain measured values ($X_M$) are summed-up during a prescribed repetition number (N) and therefrom an average value ($\overline{X}$) is formed, which represents an average reference baseline value ($\overline{X}_R$) for further current strain measured values ($X_M$) and therefrom an absolute limit value range is calculated through prescription of a permissible deviation ($n_{GW\%}$) for each reference base value ($X_R$).

6. The method for evaluation of measured values according to claim 5, characterized in that the current strain measured value ($X_M$) is detected after the repetition of a prescribed number (N) of loading conditions that are provided for the formation of the average reference base value ($\overline{X}_R$) and is compared with the average reference base value ($\overline{X}_R$) by the evaluating apparatus (9), and upon exceeding the determined limit value range this is evaluated as material fatigue manifestation for the applicable measuring circuit.

7. The method for evaluation of measured values according to claim 1, characterized in that the evaluating apparatus (9), after the detection of at least two different load values ($y_i$) of a certain loading element (3) and the allocated strain measured values ($X_i$) caused thereby, forms therefrom linearity coefficients ($K_L$) and upon a deviation that exceeds a prescribed limit range evaluates this as material fatigue manifestation.

8. The method for evaluation of measured values according to claim 1, characterized in that from the strain measured values ($X_i$) of a prescribed number (N) of repetition measured values of a certain loading condition, in the evaluating apparatus (9), a reference standard deviation ($\sigma_R$) is calculated therefrom, and an allocated limit value range is calculated therefrom through prescription of a permissible deviation ($n_{GW\%}$) for each reference standard deviation ($\sigma_R$).

9. The method for evaluation of measured values according to claim 8, characterized in that in the evaluating apparatus (9), after repetition of a certain loading condition, which follows at least after the prescribed number (N) for the formation of the reference standard deviation, with the aid of the current strain measured value ($X_i$) a current standard deviation ($\sigma$) is calculated, which is compared with the reference standard deviation ($\sigma_R$) and is evaluated as material fatigue manifestation upon exceeding of the associated limit value range.

10. The method for evaluation of measured values according to claim 1, characterized in that from the strain measured values ($X_i$) of a prescribed number (N) of repetition measured values of a certain loading condition, in the evaluating apparatus (9), the reference standard deviation ($\sigma_R$) is calculated therefrom and forms a limit value range for the standard deviation with the aid of a prescribed multiple (n) of the reference standard deviation ($\sigma_R$).

11. The method for evaluation of measured values according to claim 10, characterized in that thereafter from the prescribed number (N) of previous repetition measured values ($X_i$), continuously a sliding average value ($\overline{X}$) and therefrom a current standard deviation ($\sigma$) is calculated, which then represents a trend, which is evaluated as material fatigue manifestation upon exceeding of the limit value range.

12. The method for evaluation of measured values according to claim 1, characterized in that for each detected measured value ($X_i$) an absolute measuring inaccuracy deviation is calculated and this is compared with the respective absolute limit value range, whereby the detected measured value ($X_i$) is only taken into consideration for the evaluation when the limit value range is larger than the measuring inaccuracy deviation.

13. The method for evaluation of measured values according to claim 1, characterized in that:
immediately after the start of the testing method:
at first an evaluation according to an individual measured value comparison takes place characterized in that, according to the detected strain measured values ($X_M$) for each loading condition, from the first existing current measured values for each measuring circuit these are evaluated as reference measured values ($X_R$) and therefrom an absolute limit value range is calculated for each reference value ($X_R$) through prescription of a permissible deviation ($n_{GW\%}$);
and for corresponding number (N) of repetition measurements of certain loading conditions:
a baseline comparison takes place, characterized in that, for the repetition of certain loading conditions, the associated strain measured values ($X_M$) are summed-up during a prescribed repetition number (N) and therefrom an average value ($\overline{X}$) is formed, which represents an average reference baseline value ($\overline{X}_R$) for further current strain measured values ($X_M$) and therefrom an absolute limit value range is calculated through prescription of a permissible deviation ($n_{GW\%}$) for each reference base value ($X_R$),
a linearity evaluation takes place, characterized in that the evaluating apparatus (9), after the detection of at least two different load values ($y_i$) of a certain loading element (3) and the allocated strain measured values ($X_i$) caused thereby, forms therefrom linearity coefficients ($K_L$) and upon a deviation that exceeds a prescribed limit range evaluates this as a material fatigue manifestation,
a formation of the reference values according to the standard deviation ($\sigma$) takes place, characterized in that from the strain measured values ($X_i$) of a prescribed number (N) of repetition measured values of a certain loading condition, in the evaluating apparatus (9), a reference standard deviation ($\sigma_R$) is calculated therefrom, and an allocated limit value range is calculated therefrom through prescription of a permissible deviation ($n_{GW\%}$) for each reference standard deviation ($\sigma_R$), and
a trend evaluation takes place, characterized in that from the strain measured values ($X_i$) of a prescribed number (N) of repetition measured values of a certain loading condition, in the evaluating apparatus (9), the reference standard deviation ($\sigma_R$) is calculated therefrom and forms a limit value range for the standard deviation with the aid of a prescribed multiple (n) of the reference standard deviation ($\sigma_R$), and thereafter from the prescribed number (N) of previous repetition measured values ($X_i$), continuously a sliding average value ($\overline{X}$) and therefrom a current standard deviation ($\sigma$) is calculated, which then represents a trend, which is evaluated as a material fatigue manifestation upon exceeding of the limit value range.

14. The method for evaluation of measured values according to claim 1, characterized in that corresponding to certain definitions of objects, at least two different evaluation methods are combined with one another by the evaluating apparatus (9) in such a manner so that the evaluation takes place as simultaneously as possible with the current measured value detection, the evaluation is sufficiently accurate and fulfills the necessary safety requirements for air travel.

15. A method of determining an occurrence of a material fatigue manifestation in at least one of plural aircraft components of an aircraft due to material fatigue during fatigue testing of said aircraft components, comprising the steps:
   a) by externally acting on said aircraft with a plurality of externally acting loading elements, imposing on said aircraft components a plurality of prescribed loading conditions in successive loading cycles, thereby causing strains in said aircraft components;
   b) detecting said strains with strain gages arranged on said aircraft components, and with said strain gages producing strain gage outputs representative of said strains;
   c) evaluating said strain gage outputs to determine therefrom measured strain values respectively successively in said successive loading cycles and respectively allocated to said strain gages;
   d) for each one of said loading conditions for each one of said strain gages, respectively establishing a reference value based on at least a first one of said measured strain values arising in a first one of said successive loading cycles;
   e) specifying a permissible deviation;
   f) for each said reference value, determining an absolute limit value range based on said permissible deviation relative to said reference value;
   g) comparing said measured strain values to said absolute limit value range, respectively for each one of said loading conditions for each one of said strain gages; and
   h) if said comparing in said step g) determines that at least one of said measured strain values falls outside of said absolute limit value range, then in response thereto determining, signaling or indicating that a material fatigue manifestation has occurred in at least one of said aircraft components.

* * * * *

UNITED STATES PATENT AND TRADEMARK OFFICE
CERTIFICATE OF CORRECTION

| | | |
|---|---|---|
| PATENT NO. | : 7,930,112 B2 | Page 1 of 1 |
| APPLICATION NO. | : 11/919107 | |
| DATED | : April 19, 2011 | |
| INVENTOR(S) | : Johannes Mattes | |

It is certified that error appears in the above-identified patent and that said Letters Patent is hereby corrected as shown below:

Column 7,
Line 51, after "value", replace "Y" by -- $\overline{Y}$ --;
Lines 59-63, replace the formula by $$K_L = \frac{\sum_{i=1+k}^{N}(x_i - \overline{x}) \times (y_i - \overline{y})}{\sqrt{\sum_{i=1+k}^{N}(x_i - \overline{x})^2 \times \sum_{i=1+k}^{N}(y_i - \overline{y})^2}}$$

--                                                                                --

Column 8,
Line 23, after "deviation", replace "a" by --σ--;

Column 9,
Line 57, after "example ± 0.9", replace "mv/V" by --mV/V--.

Signed and Sealed this
Eighth Day of May, 2012

David J. Kappos
*Director of the United States Patent and Trademark Office*